(12) United States Patent
Carroll

(10) Patent No.: US 6,527,442 B2
(45) Date of Patent: Mar. 4, 2003

(54) INTEGRATED SENSOR HOLDER FOR DENTAL IMAGING

(75) Inventor: Seamus Carroll, Cold Spring, NY (US)

(73) Assignee: AFP Imaging Corporation, Elmsford, NY (US)

(*) Notice: Subject to any disclaimer, the term of this patent is extended or adjusted under 35 U.S.C. 154(b) by 128 days.

(21) Appl. No.: 09/765,538

(22) Filed: Jan. 19, 2001

(65) Prior Publication Data

US 2001/0055368 A1 Dec. 27, 2001

Related U.S. Application Data

(63) Continuation-in-part of application No. 09/711,798, filed on Nov. 13, 2000, which is a continuation-in-part of application No. 09/603,395, filed on Jun. 26, 2000.

(51) Int. Cl.[7] .................................................. H01J 31/50
(52) U.S. Cl. ........................................ 378/189; 378/169
(58) Field of Search ................................. 378/189, 169, 378/168, 98.8, 191; 250/370.11

(56) References Cited

U.S. PATENT DOCUMENTS

| | | | | |
|---|---|---|---|---|
| 5,331,166 A | * | 7/1994 | Yamamoto et al. | 250/370.11 |
| 5,434,418 A | * | 7/1995 | Schick | 250/370.11 |
| 5,510,623 A | * | 4/1996 | Sayag et al. | 250/370.11 |
| 5,677,537 A | | 10/1997 | Pfeiffer | 250/370.09 |
| 5,844,961 A | * | 12/1998 | McEvoy et al. | 378/98.8 |
| 6,042,267 A | * | 3/2000 | Muraki et al. | 378/169 |
| 6,169,781 B1 | | 1/2001 | Doebert et al. | 378/98.8 |
| 6,405,926 B1 | * | 6/2002 | Yomogida et al. | 235/462.46 |

FOREIGN PATENT DOCUMENTS

JP 72-80944 10/1995 ............. G01T/1/20

* cited by examiner

Primary Examiner—Drew A. Dunn
Assistant Examiner—Irakli Kiknadze
(74) Attorney, Agent, or Firm—Cooper & Dunham LLP (57) ABSTRACT

An X-ray imaging system comprising an X-ray image sensor, a computing device, and an interface package is provided. The interface package includes a first interface to the X-ray image sensor and a second interface to the computing device. A sensor holder is integrated with the interface package to hold the X-ray image sensor when the sensor is not being used. The interface package may include an electrical cable coupled to the interface for connecting the interface to the sensor or to the computing device. The sensor holder may be integrated with a housing of the interface package. Alternatively, the sensor holder may be integrated with a connector on the electrical cable. In other embodiments, the sensor holder may be attached to the electrical cable. The interface package may include a wireless e to a wireless sensor and/or to the computing device.

32 Claims, 10 Drawing Sheets

INTEGRATED SENSOR HOLDER FOR DENTAL IMAGING

CROSS REFERENCE TO RELATED APPLICATIONS

This application is a continuation-in-part of U.S. patent application Ser. No. 09/711,798, filed Nov. 13, 2000 and entitled "DENTAL X-RAY IMAGING SYSTEM", which is a continuation-in-part of U.S. patent application Ser. No. 09/603,395, filed Jun. 26, 2000 and entitled "TRIGGERING OF SOLID STATE X-RAY IMAGERS WITH NON-DESTRUCTIVE READOUT CAPABILITY".

BACKGROUND OF THE INVENTION

The present invention relates to an X-ray imaging system. In particular, the invention relates to an integrated sensor holder in a dental X-ray imaging system.

X-ray sensors used in a dental X-ray imaging system are replacing film as the preferred tool for dentists to obtain X-ray images of teeth. An intra-oral sensor is inserted into the patient's mouth and positioned behind the tooth/teeth to be imaged, and then the tooth/teeth to be imaged is irradiated with X-rays from an X-ray source. Next, the imaging sensor transmits electronic signals typically via an electrical cable extending from the sensor to an external image processing and memory unit (typically, a personal computer) in the X-ray imaging system which processes and displays on a computer monitor a corresponding image. In this manner, X-ray images can be produced directly on location without substantial delay and are immediately visible on the computer monitor.

Since the intra-oral sensor is inserted in a patient's mouth, it is highly desirable to maintain the sensor in a sterile condition, as much as possible. A sensor holder is sometimes provided to avoid having the sensor dangle/rest in an easy-to-contaminate position. The typical sensor holder is a separate unit which must be affixed to a surface of a wall, chair or other dental apparatus. Such sensor holders detract from the portability of the sensor, particularly when there are a plurality of dental stations in a dental office and it is desired to carry the sensor to, and use the sensor at, any of the plurality of dental stations.

SUMMARY OF THE INVENTION

The present invention provides, in accordance with one embodiment, an interface for connecting an X-ray image sensor and a computing device in an X-ray image sensing system comprising, a housing, a printed circuit board in an interior of the housing, and a sensor holder integrated with the interface to hold the X-ray image sensor when the sensor is not being used. The printed circuit board may have circuitry residing thereon for receiving electronic signals supplied by the X-ray image sensor and processing the received signals to communicate the processed signals to the computing device. The printed circuit board may have circuitry residing thereon for receiving commands from the computing device for controlling the X-ray image sensor. The sensor holder may be shaped and sized to hold each of a plurality of different-sized sensors.

The present invention also provide an X-ray imaging system comprising, in accordance with one embodiment, an X-ray image sensor, a computing device, and an interface package including a first interface to the X-ray image sensor and a second interface to the computing device. A sensor holder is integrated with the interface package to hold the X-ray image sensor when the sensor is not being used. The sensor holder may be integrated in the first interface or the second interface. The X-ray imaging system may be a digital dental imaging system and the X-ray image sensor may be an intraoral sensor.

The interface package may include an electrical cable for coupling the first interface to the X-ray image sensor. The sensor holder may be attached to the electrical cable. The first interface may have a first connector and the electrical cable a second connector, the first interface and the electrical cable may be detachably coupled through mating of the first connector and the second connector, and the sensor holder may be integrated with the second connector.

The interface package may include an electrical cable for coupling the second interface to the computing device. The electrical cable may be coupled to the computing device through a USB port of the computing device. The sensor holder may be attached to the electrical cable. The second interface may have a first connector and the electrical cable a second connector, the second interface and the electrical cable may be detachably coupled through mating of the first connector and the second connector, and the sensor holder may be integrated with the second connector.

The second interface may include a wireless interface for communicating with a wireless interface in the computing device. The first interface may include a first wireless interface for communicating with a second wireless interface in the X-ray image sensor. The X-ray image sensor may be wireless and the interface may include a charger for recharging the wireless X-ray image sensor. The interface package may include a docking station for downloading data from the wireless X-ray image sensor.

BRIEF DESCRIPTION OF THE DRAWINGS

The above and numerous other objectives, features and advantages that may be achieved by the present invention would be more readily understood from the following detailed description by referring to the accompanying drawings wherein.

DETAILED DESCRIPTION OF THE INVENTION

To further explain the invention, some embodiments are described in connection with the drawings and their supporting descriptions provided below.

Figure 1A:
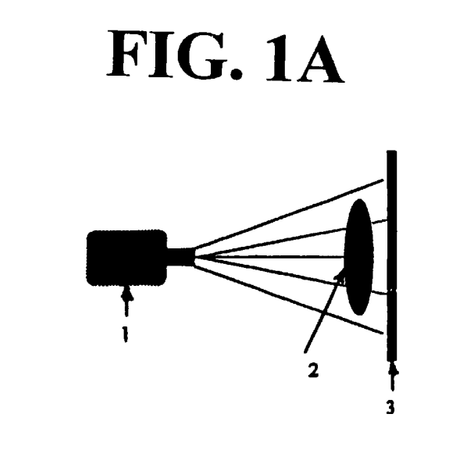
FIG. 1A shows a schematic view of an X-ray imaging system.

FIG. 1A shows an X-ray imaging system with an X-ray generator 1 emitting X-rays, and arranged to irradiate an object 2 to be imaged. Part of the X-rays are absorbed by the object 2 to be imaged. An X-ray image sensor 3 is located behind that object. The X-ray photons which pass through the object are detected by the image sensor 3.

Figure 1B:
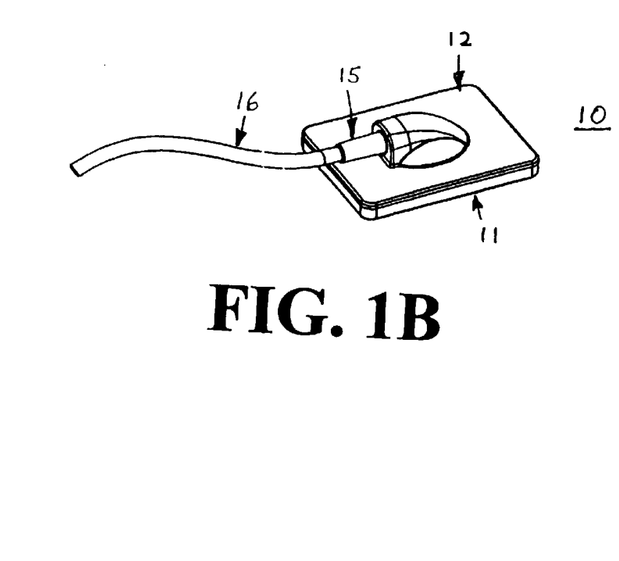
FIG. 1B shows a perspective view of a sensor capsule, according to one embodiment of the present invention.

An X-ray image sensor, according to one embodiment of the present invention, will be described with reference to FIGS. 1B and 1C. Sensor capsule assembly 10 comprises capsule bottom 11, capsule top 12, sensor 13, bobbin 14, boot 15 and electrical cable 16. The X-ray detector 13 generates and transmits electrical signals through electrical cable 16 and an interface (described below) to an image processing/computing device. As discussed further below, peripheral processing may be performed by the computing device or by circuitry coupled to the computing device.

Figure 1C:
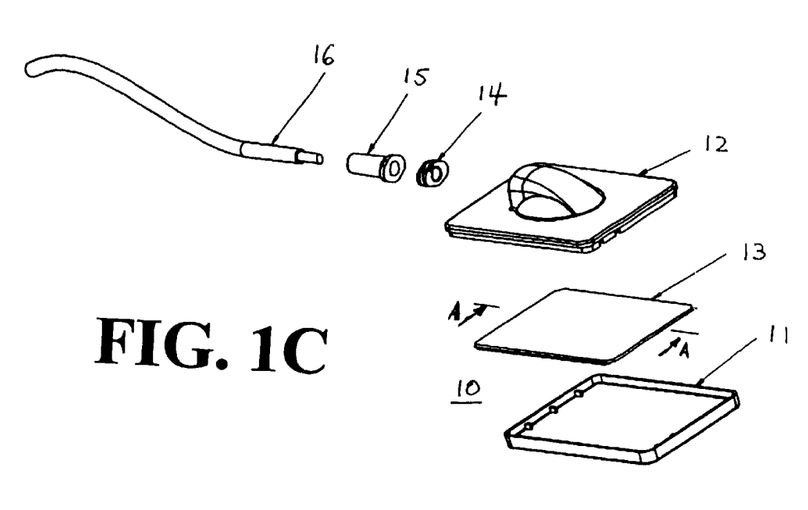
FIG. 1C shows an exploded view of the sensor capsule assembly shown in FIG. 1B.
Figure 1D:
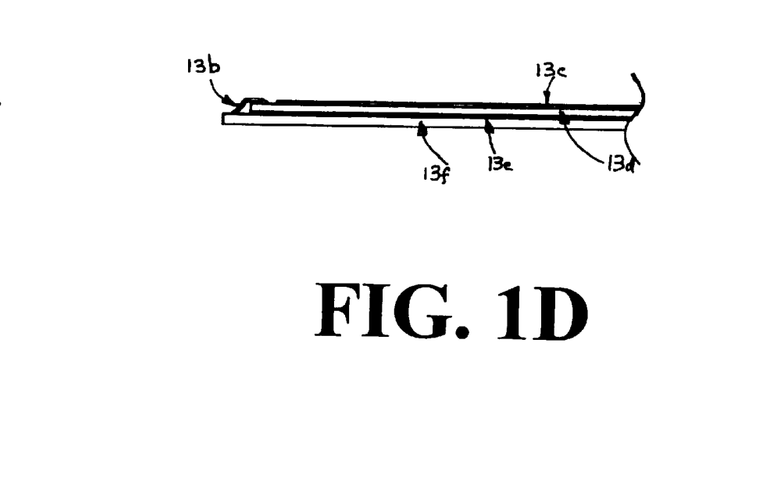
FIG. 1D shows a cross-sectional view taken along section line A—A of an X-ray sensor carrier shown in FIG. 1C.

FIG. 1D is a magnified cross sectional view of an embodiment of the X-ray detector 13 of FIG. 1C, taken from section line A—A. In the embodiment shown in FIG. 1D, the X-ray detector includes a scintillator 13c on top of a semiconductor 13d, all supported on a passivated ceramic substrate 13f. In general terms, the scintillator 13c converts X-rays into visible light while the semiconductor 13d, in turn, converts the light into electrical signals representing the image.

The scintillator layer 13c is interposed between the X-ray source and the semiconductor layer 13d, to both protect the semiconductor from unwanted X-ray exposure and to provide conversion of the X-rays to visible light for direct detection by the semiconductor. X-ray-to-light converting materials that may be used for the scintillator include gadolinium oxysulphide, cesium iodide, cadmium tungstate, cadmium telluride, cadmium sulfide, calcium tungstate, zinc sulfide and zinc cadmium sulfide. Scintillating glass, such as for example terbium glass, or scintillating optical fibers also may be used. The scintillator 13c is positioned to be directly exposed to the X-rays which readily pass through a protective housing formed by capsule bottom 11 and capsule top 12.

The semiconductor 13d may be one of a number of semiconductor devices, including charge coupled devices (CCD), charge injection devices (CID), complementary metal oxide semiconductor (CMOS), etc., that have been used for imaging sensors which convert an optical image into an electronic signal. The semiconductor 13d preferably comprises an array of pixels and an integrated signal amplifier. The electrical signals produced by the semiconductor 13d are conveyed to the electrical cable 16 via conductive lead 13b. The conductive lead 13b also may convey electrical power and control signals from the computing device and/or interface (described below) to the semiconductor 13d.

The semiconductor 13d may sit on top of an X-ray absorption layer 13e. Absorption layer 13e absorbs any X-rays which are not converted by the scintillator 13c, to prevent those X-rays from hitting the patient, and absorbs any back-scattered radiation. X-ray absorbing materials that may be used for layer 13e include, for example, lead and tungsten.

The entire X-ray detector is enclosed in a protective enclosure formed by capsule bottom 11 and capsule top 12, which, along with bobbin 14 and boot 15, protects the X-ray detector from shock and moisture, while being permeable to X-ray radiation. Capsule bottom 11 and capsule top 12 may be made from, for example, aluminum or any one of many formulations of plastic known in the art.

X-ray imaging systems may be used in assorted digital X-ray imaging applications, including digital dental X-ray imaging to display and record dental radiographic images using a conventional dental X-ray source and an image processing/computing device. The digital X-ray imaging system may include hardware and software components.

Figure 2A:
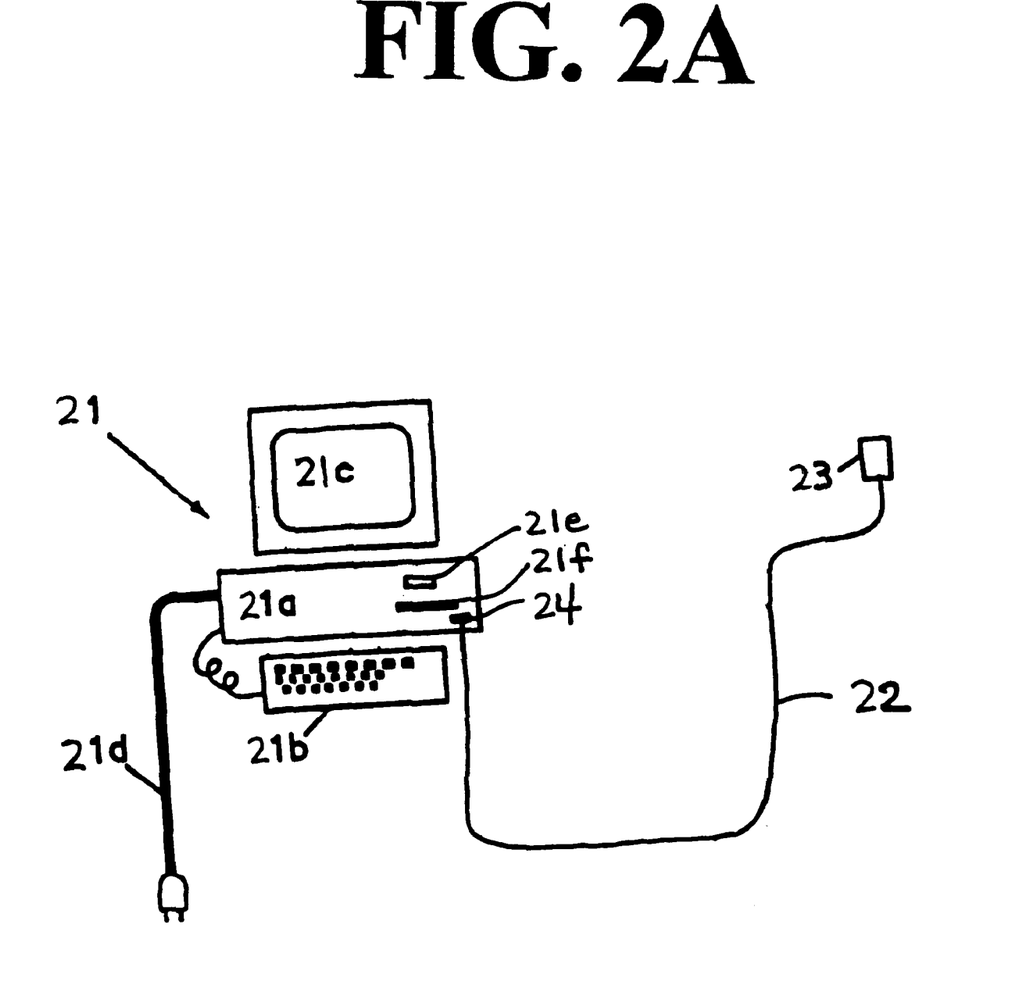
FIG. 2A shows a schematic view of an X-ray imaging system.
Figure 2B:
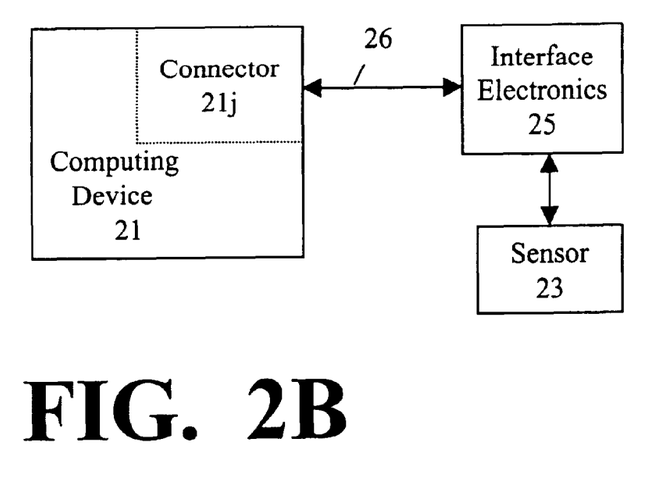
FIG. 2B shows a block diagram of an X-ray imaging system, according to an embodiment of the present invention.

FIGS. 2A and 2B show some of the hardware components that may be included in the system. The hardware components may include computing device 21, image sensor 23, and interface electronics and an electrical cable 22 to link the sensor to the computing device.

The interface electronics will be further described below. Interface electronics and connector 24, in the embodiment shown in FIG. 2A, are integrated with the packaging of computer 21. The user may disconnect the sensor from the computing device by unplugging a connector (see also, e.g., FIG. 8H) at the end of the electrical cable from the mating connector integrated with the computer, to switch to alternate sensor assemblies.

In another embodiment (FIG. 2B), there is an intermediate connection point 25 between sensor 23 and computing device 21. Interface electronics 25 is connected to computing device 21 via a standard-type, e.g., USB (Universal Serial Bus), electrical cable/connector 26. While the user could disconnect the sensor from the computing device by detaching the (e.g., USB) electrical cable/connector from a USB port 21j of the computing device if desired, USB connectors, when the computing device is a personal or workstation computer, usually are provided on the back of the computer and therefore may be inconvenient to access. In addition, many low cost computing devices use low quality USB connectors which may fail in as little as one hundred (or even less) connection cycles. Thus, it is desirable to leave the USB cable connected to the computing device and have a high reliability interface 25 to connect the sensor to the computing device through electrical cable 26. Alternatively, cable 26 may be hard-wired to interface 25 (see also, e.g., FIGS. 8A, 8C, 8D and 8G), and in such embodiments, the sensor may be disconnected from the computing device by disconnecting the connector at the end of cable 26 from the computing device.

Interface 25 may be, for example, a high reliability USB interface or a FireWire. Interface 25 may comprise a pair of mating connectors which may be detachable or permanently attached, as described below.

Sensors of different sizes may be provided. In a dental application, a sensor that may be inserted into the patient's mouth preferably is provided. In one exemplary embodiment for a dental application, two sensors, having the approximate dimensions of 42 mm×30 mm×5 mm and 34 mm×25 mm×5 mm, respectively, are provided. Dimensions different from these exemplary dimensions may be selected, according to application and/or to accommodate an ergonomic or stylistic design. Image sensor 23 may be inserted into the patient's mouth and positioned to record the radiographic image of the teeth. The sensor may be connected to the computing device via an electrical cable with, for example, a standard USB computer interface in one embodiment.

Figure 2C:
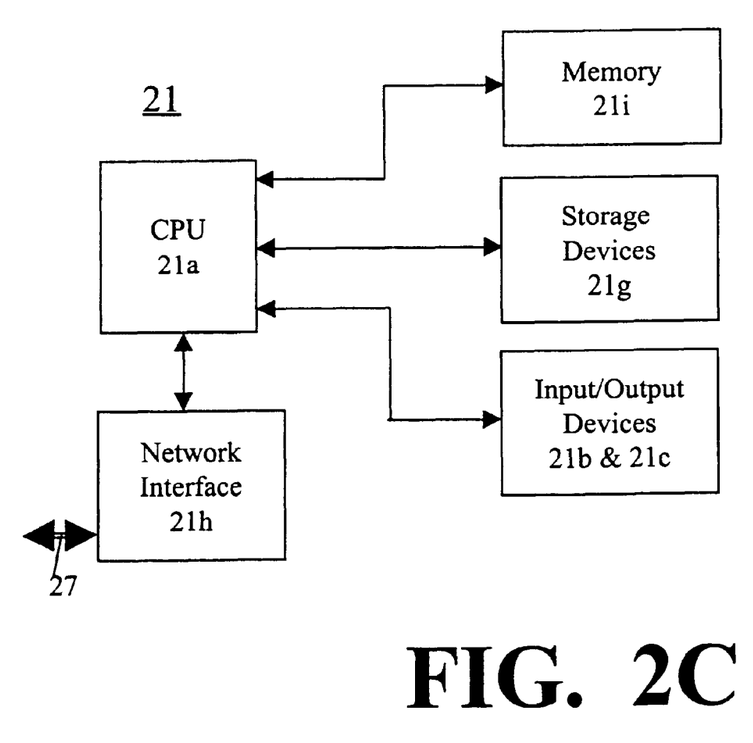
FIG. 2C shows a block diagram of a computing device which may be used in the X-ray imaging systems shown in FIGS. 2A and 2B.

Computing device 21 typically is a personal computer (FIG. 2A) and may have the components shown in FIGS. 2A–2C. Computing device 21, alternatively, may be, for example, a workstation computer, a notebook computer, or a handheld computing device, e.g., personal digital assistant.

Computing device 21 comprises CPU 21a, input devices 21b, output devices 21c, memory 21i and one or more storage drives 21g, and may optionally also include power cord 21d and network interface 21h. The storage drives may include, for example, floppy disk drive 21e, CD (or DVD) drive 21f and a hard disk, etc.

The input/output devices may include a keyboard, mouse, microphone, track ball, stylus, monitor, printer/plotter, touch screen, speaker, etc., plus the appropriate device drivers and user interface software.

Network interface 21h may be included for connecting to a network 27, which may be any one or a combination of the Internet, an intranet, an extranet, a LAN (local area network), a WAN (wide area network), a wireless network and other networks. Network interface 21h includes the appropriate units for interfacing with the network 27, including, for example, Ethernet card, modem, wireless modem, etc.

Software components in the dental X-ray imaging system may include a graphical user interface to control the hardware, image management functions and interfaces to other dental software packages. The software components may also include assorted device drivers, including a wireless communication driver if a wireless interface is provided.

The software components may be stored on a floppy disk, CD or another storage medium, and installed on the computing device. The software components alternatively (or also) may be communicated through the network interface via a network, such as the Internet, and/or a wireless transmission medium. Further, each software component may comprise one or more segments, subsets of which are retrieved, from the computer hard disk or via the network or transmission medium, as need arises.

The functions of the system may depend on the hardware and software implementation. The functions may be combined/split or otherwise modified to ease the design, manufacture and serviceability of the system. Thus, image capture control functions may be implemented by, for example, a combination of software and hardware components. The following exemplary image capture functions may be provided: initialize the system, i.e. communicate with the sensor over the USB or other standard computer interface (or wireless means) and wake it up if required; obtain system status; prepare for exposure by commanding the hardware to enter a wait-for-exposure mode and erase image currently stored in system memory; detect capture of an image, and signal client software that an image has been captured and is ready for upload; initialize image data transfer, and send command to start upload of image data to the system (the image data may be sent as a complete image or streamed as available); a command is sent from client to the system to exit wait-for-exposure mode and enter standby mode; and retrieve integration time.

Figure 3:
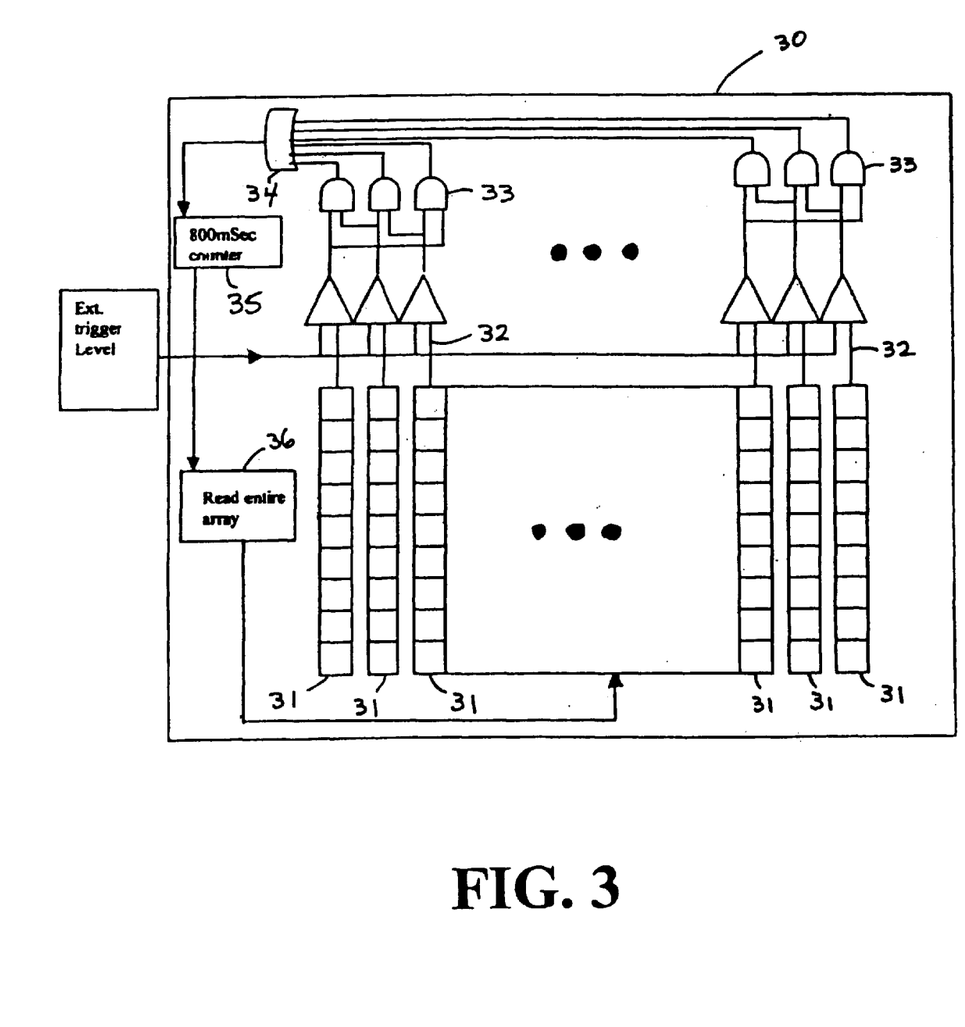
FIG. 3 shows a schematic view of image capture circuitry in an X-ray image sensor, according to one embodiment of the present invention.

FIG. 3 shows image capture circuitry 30 in an X-ray image sensor. The X-ray image sensor has a plurality of columns 31 of pixels, although only two sets of columns selected as reference pixels are shown in FIG. 3. Circuitry 30 also includes Boolean logic units 33 and 34, counter 35, readout block 36 and memory 37.

Preferably all the charge in each of the selected columns is averaged together for one low noise signal 32 per column. The columns in each set are logically compared to determine whether at least two out of three columns of summed charges in each set exceeds a predetermined threshold level. Boolean logic units 33 and 34 are used to verify that two out of three columns have exceeded the predetermined threshold level. The Boolean logic units also eliminate (i) any individual pixel defects from lowering device yields and (ii) lower frequency noise sources. Either set of three columns may trigger a counter 35 that then would count down a minimum of 800 milliseconds in this embodiment before causing one frame of video to be read out by block 36. The selected columns of pixels are reset at a 10 Hz frame rate to eliminate any possibility of dark current build up while waiting for an X-ray event.

Additional image capture features and imager trigger features are described in U.S. patent applications Ser. Nos. 09/711,798, filed Nov. 13, 2000, and 09/603,395, filed Jun. 26, 2000, which are incorporated herein by reference.

Figure 4A:
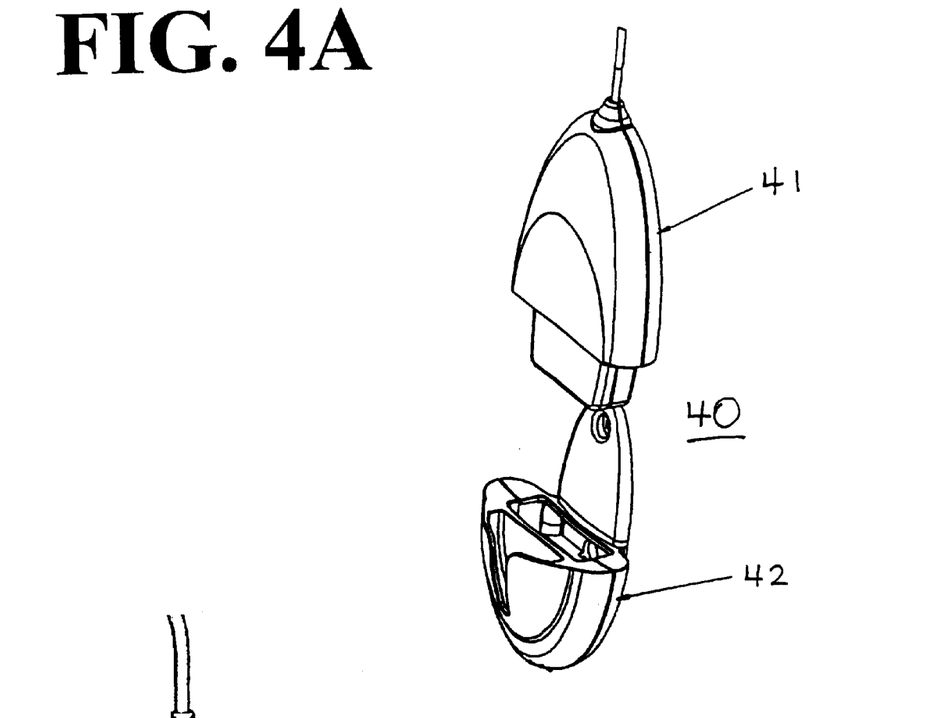
FIG. 4A shows an exploded view of an interface assembly, with an integrated sensor holder in a dental X-ray imaging system, according to one embodiment of the present invention.
Figure 4B:
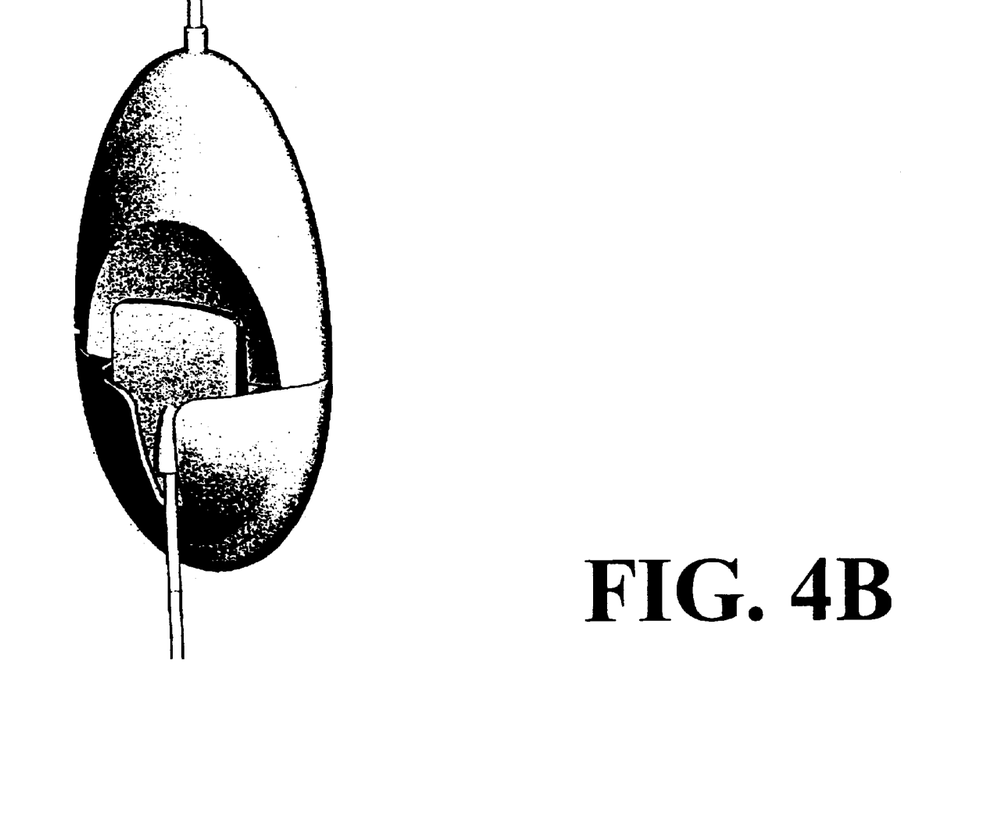
FIG. 4B shows a perspective view of the interface assembly shown in FIG. 4A, with a sensor resting in the sensor holder.

An interface assembly, according to one embodiment of the present invention, is shown in FIG. 4A. Interface assembly 40 comprises an interface module 41 and an interface base 42. The interface module serves as an interface to the sensor, while the interface base serves as an interface to the computing device and also may serve as a docking station for the sensor. When the sensor is not in use, the sensor may be placed in a sensor holder integrated with the interface base (FIG. 4B).

Figure 5A:
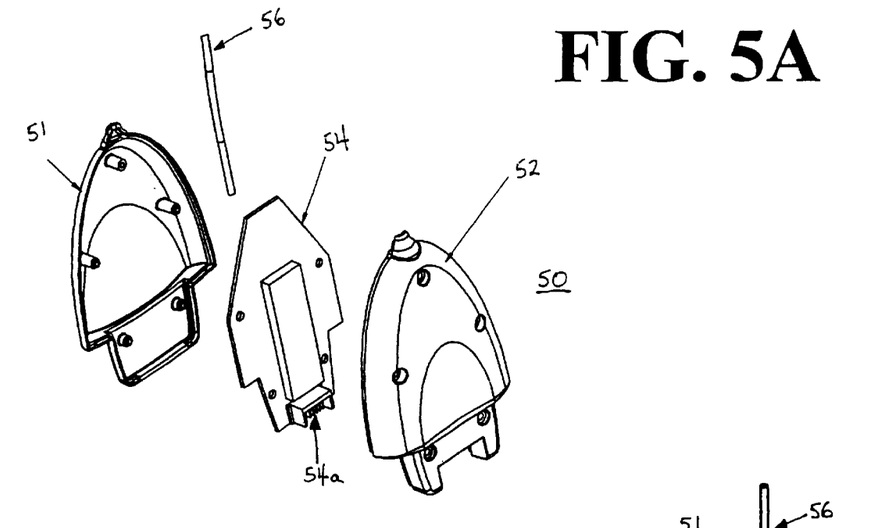
FIG. 5A shows an exploded view of an interface module, according to one embodiment, in the interface assembly shown in FIGS. 4A and 4B.
Figures 5B, 5C:
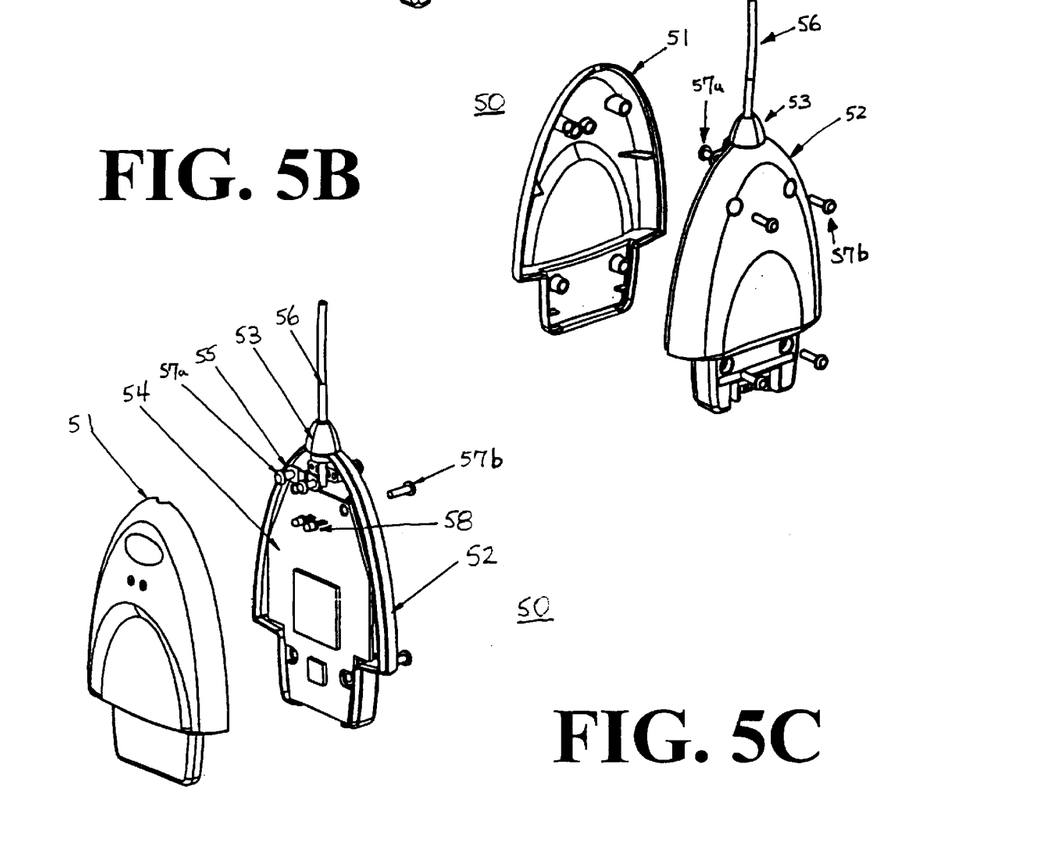
FIGS. 5B and 5C show respective exploded views of an interface module, according to another embodiment, in the interface assembly shown in FIGS. 4A and 4B.

Some embodiments of the interface module are shown in FIGS. 5A–5C. Interface module assembly 50 comprises shell cover 51, shell bottom 52, module strain relief 53, printed circuit board 54, cable strain relief 55, electrical cable 56, screws 57a and 57b, and LEDs (light-emitting diodes) 58.

The shell cover 51 and shell bottom 52 provide a housing for the printed circuit board 54. A plurality of screws 57b may be provided to secure the shell cover 51, shell bottom 52 and printed circuit board 54 together. Screws 57a secure cable strain relief 55. The embodiment shown in FIG. 5A and the embodiment shown in FIGS. 5B and 5C differ in the positioning of the screws, which is a matter of designer's choice. LEDs 58 are provided in the embodiment shown in FIGS. 5B and 5C as an indicator that the interface module is properly connected, receiving power and otherwise operational.

The printed circuit board 54 has circuitry thereon for receiving and processing electronic signals received from the image sensor through electrical cable 56, and also has a male-type connector 54a at the bottom of the board.

Figures 6A, 6B, 6C:
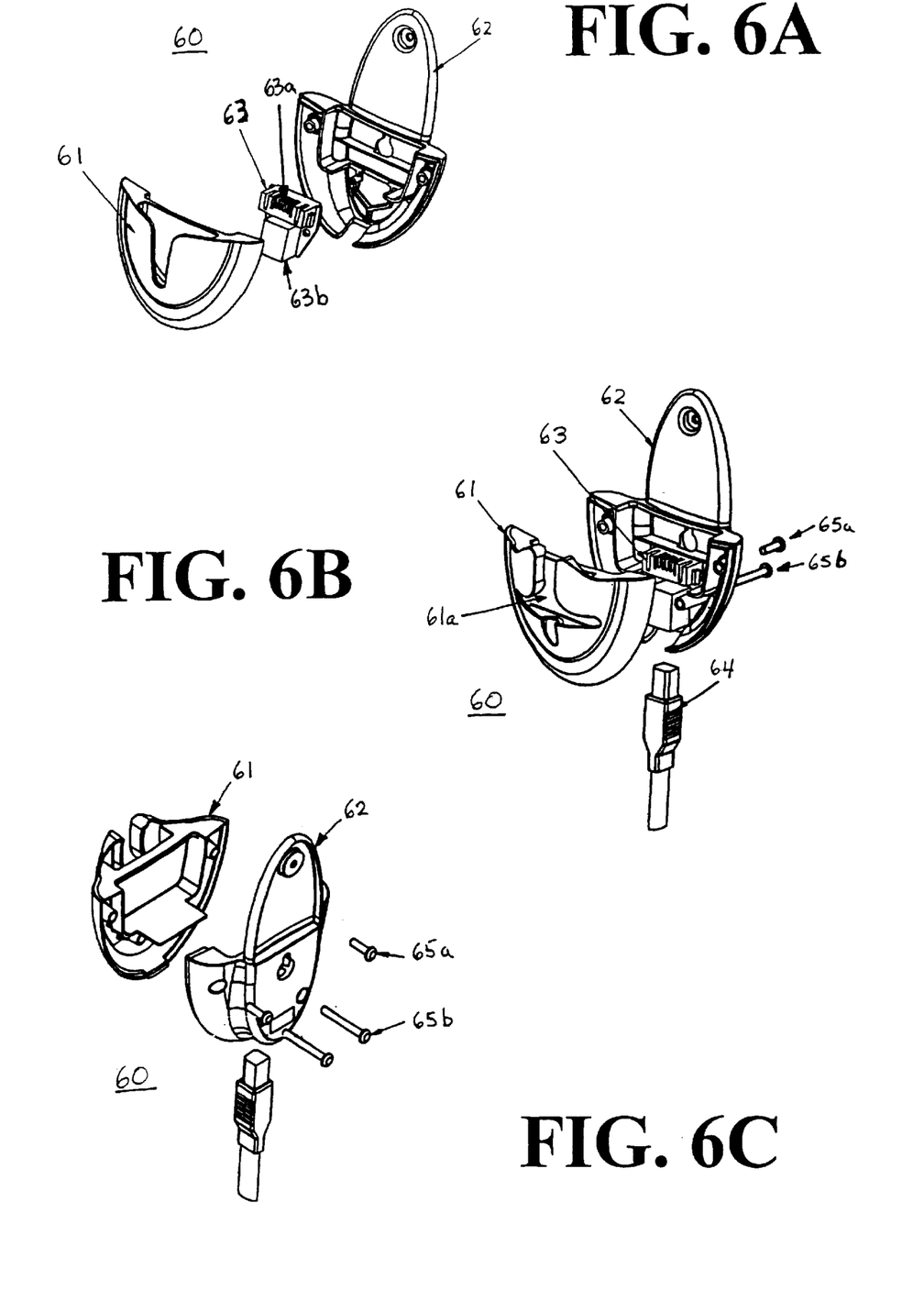
FIG. 6A shows an exploded view of an interface base, according to one embodiment, in the interface assembly shown in FIGS. 4A and 4B.
FIGS. 6B and 6C show respective exploded views of an interface base, according to another embodiment, in the interface assembly shown in FIGS. 4A and 4B.

An interface base is shown in FIGS. 6A (one embodiment) and 6B–6C (another embodiment). Interface base assembly 60 comprises front cover 61, base back 62, printed circuit board 63, cable 64 and screws 65*a* and 65*b*.

The front cover 61 and base back 62, secured together by screws 65*a* and 65*b*, provide a housing for printed circuit board 63. Printed circuit board 63 has a female-type connector 63*a* which mates and becomes electrically coupled with male connector 54*a* of printed circuit board 54, when interface base 50 and interface module 60 are brought together. Printed circuit board 63 also has a connector 63*b* for coupling to electrical cable 64, which may be, for example, a USB cable, and also has circuitry residing thereon for receiving commands from the computing device through cable 64 for controlling the X-ray image sensor.

The processing performed by the circuitry in the interface (module and/or base) includes buffering data received from the sensor and may also include buffering command signals from the computing device. The circuitry may also perform data rate adjustment and other peripheral processing. For example, the received data may be stored at one rate (corresponding to the data rate of the received data), in a storage device comprising one or more buffers, memories, etc., and the stored data may be read out from the storage device at a second rate (corresponding to the data rate that the computing device expects). The processing may also include analog-to-digital conversion and/or serial-to-parallel conversion (and/or parallel-to-serial conversion), which are well known in the art and thus will not be discussed in detail here.

Figure 7A:
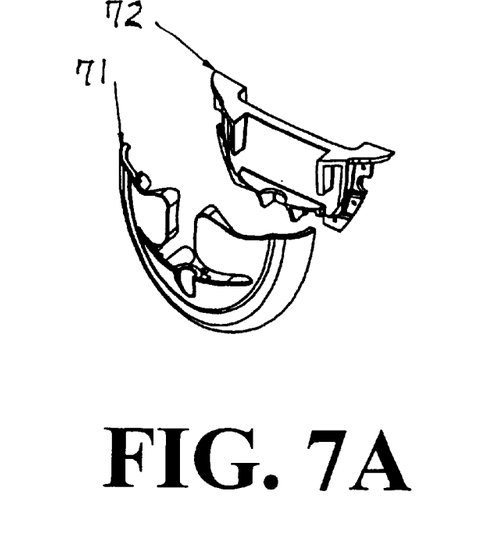
FIGS. 7A and 7B show respective exploded views of a front cover assembly, according to one embodiment, in the interface base shown in FIGS. 6A–6C.
Figure 7B:
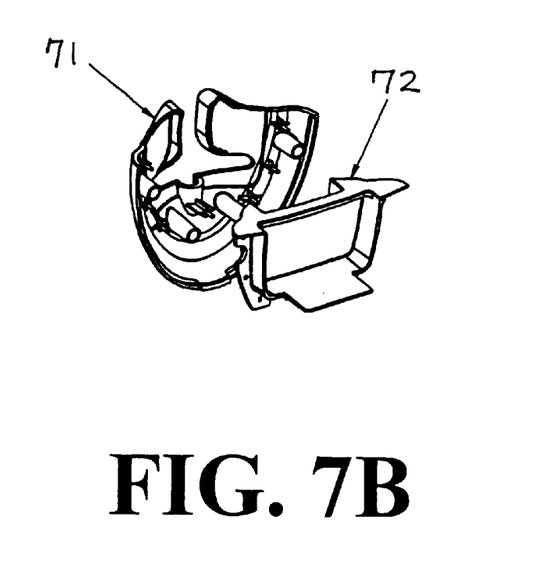

Each embodiment of the interface base shown in FIGS. 6A, 6B and 6C houses support electronics and includes an integrated sensor holder. The built-in sensor holder provides a place to store the X-ray image sensor when the sensor is not in use. FIGS. 6A–6C show embodiments in which the sensor holder is integrated in the front cover 61. The two embodiments of the interface base differ in the shape of slot 61*a* in the front cover 61. Slot 61*a* and the sensor holder are preferably sized and shaped to accommodate sensors of different shapes and sizes. Front cover 61 may be a single molded piece or an assembly. FIGS. 7A and 7B show a front cover assembly comprising cover pouch 71 and cover top 72 mated face-to-face to the pouch.

While some embodiments of the present invention have been described in detail above, it should be understood that the invention is not limited to the precise embodiments described.

For example, in other embodiments, the sensor holder may be attached to one of the electrical cables (see, e.g., FIGS. 8C, 8G and 8H), connectors (see, e.g. FIGS. 8B and 8D) or other assemblies which may or may not house support electronics.

Figure 8A:
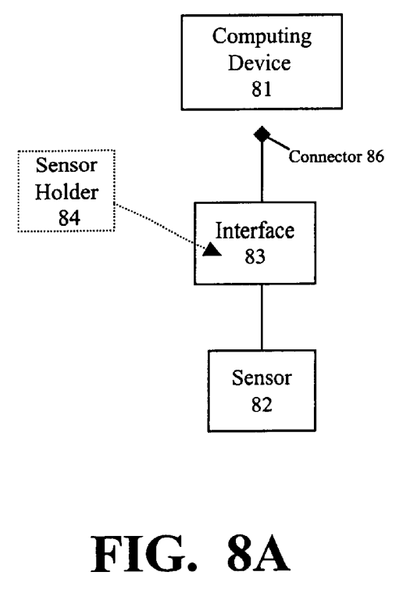
FIGS. 8A–8H show schematic views of respective exemplary embodiments of dental X-ray imaging systems, in accordance with the present invention.
Figure 8B:
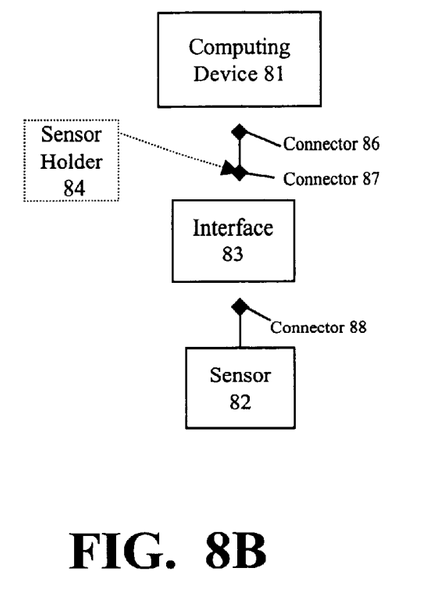
Figure 8C:
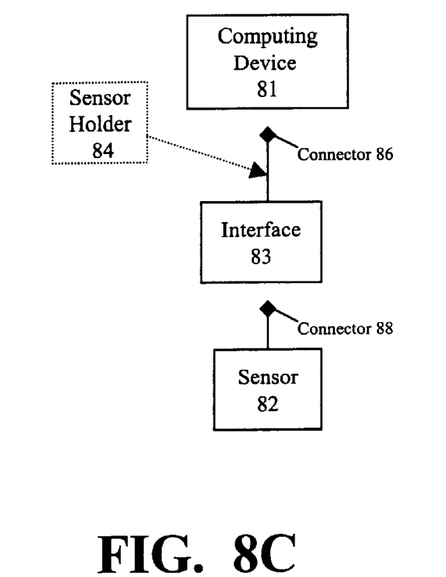
Figure 8D:
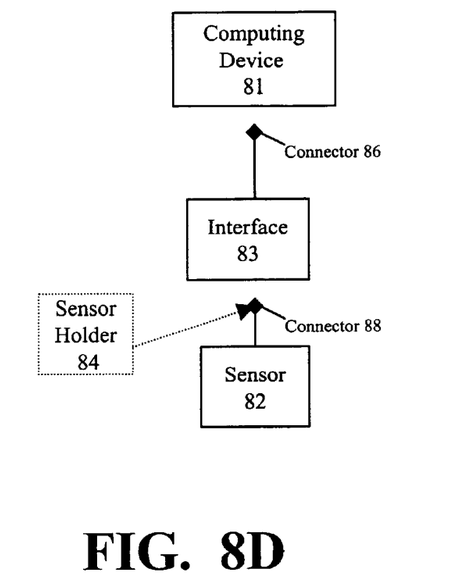
Figure 8E:
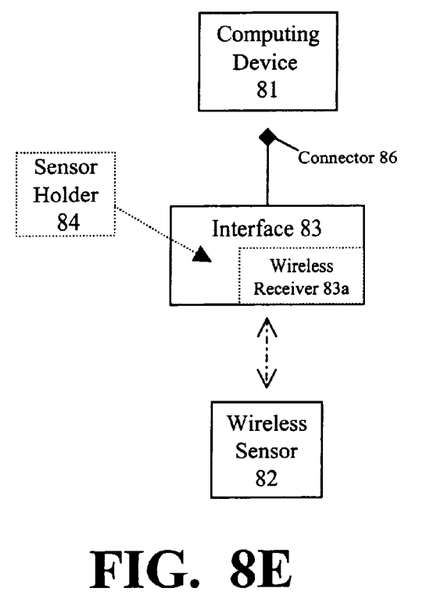

In another embodiment, the interface electronics and connector optionally may include a wireless interface for communicating with the image sensor through a wireless communication link (see, e.g., FIG. 8E). One of a number of wireless interfaces (e.g., Bluetooth), such as for an infrared optical link or radio frequency (e.g., spread spectrum RF) link, known in the art may be used. In such an embodiment, the X-ray image sensor also is provided with a wireless interface.

Figure 8F:
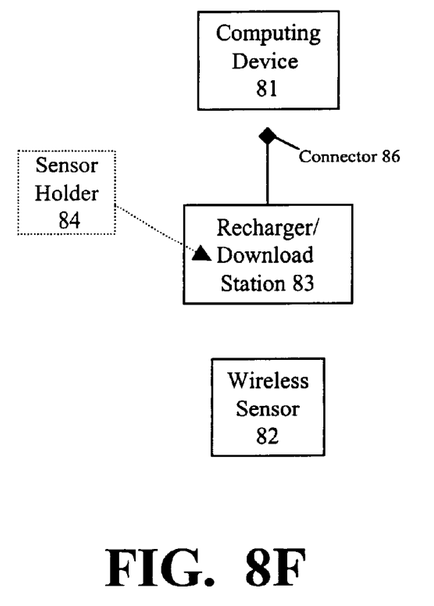

The wireless sensor may have, in one embodiment, a rechargeable battery for powering the sensor, which is placed in a recharger between uses. In another embodiment, the sensor has a capacitor which, instead of or along with a battery, stores the energy. When the sensor is removed from the charger and placed in the patient's mouth, the X-rays would trigger the sensor and discharge the capacitor, while one or more images would be held in memory on the sensor. Then, the sensor may be placed into a charger cradle, which may be integrated in the interface packaging. The charger cradle also may function as a data download (docking) station. When the image data is downloaded, the sensor is cleared and the charge storage device is recharged for the next use. The recharger/download station also serves as a sensor holder (see, e.g. FIG. 8F).

Other charge storage devices that are able to provide the power required by the sensor may be integrated with the wireless sensor. Each of the charge storage devices described above may be charged by the recharger through direct electrical connection or by inductive charging (see, e.g., U.S. Pat. No. 5,959,433).

Also, the interface package may be coupled to the computing device through a wireless (e.g., Bluetooth) interface rather than an electrical cable. Thus, connector 63*b* of the interface base assembly 60, for example, may be replaced by such a wireless interface. The computing device, of course, would have a complementary wireless interface. Such an interface package may independently be powered by a battery or power supply.

The sensor holder is integrated with the interface base in some embodiments described above. Alternatively, the sensor holder may be integrated with the interface module. As another alternative, the sensor holder may be an assembly attached to the electrical cable connecting the interface to the computing device (see, e.g., FIG. 8C).

Figure 8G:
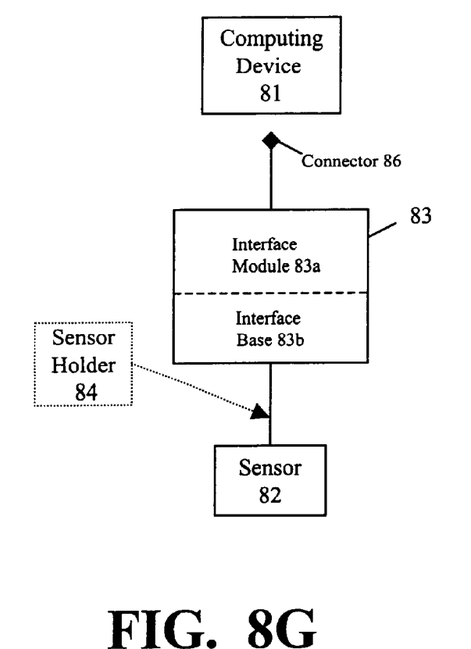
Figure 8H:
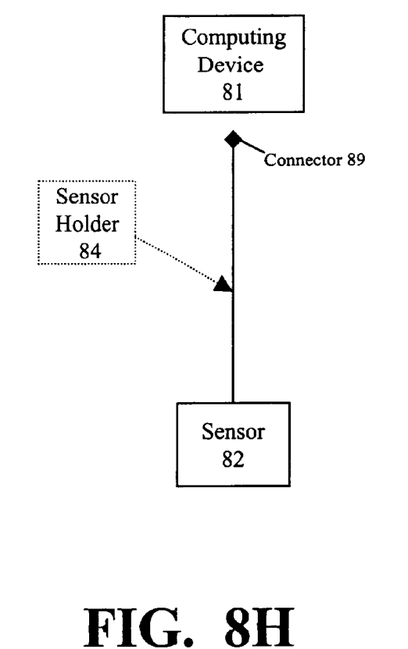

In yet another embodiment, the sensor holder may be attached to or integrated with a cable connector (see, e.g., FIGS. 8B and 8D) or one of the electrical cables (see, e.g., FIGS. 8C and 8G), for example, when no interface package housing interface electronics is provided (see, e.g., FIG. 8H).

Further, the interface package in some of the embodiments described above includes an interface module assembly and an interface base assembly detachably joined by respective mating connectors. The interface, alternatively, may be a single assembly housing a single printed circuit board. The single printed circuit board has circuitry residing thereon and may have at one end a connector to which an electrical cable connecting the interface package to the sensor may be detachably mated. The single printed circuit board may also have a connector for coupling the interface to an electrical cable which connects the interface to the computing device.

In another embodiment the electrical cable connecting the interface to the sensor is hard-wired to the interface (see, e.g., FIGS. 8A and 8G). Similarly, the electrical cable connecting the computing device and the interface may be hard-wired to the interface (see, e.g. FIGS. 8A, 8C and 8D). In yet another embodiment, both electrical cables have connectors for mating with respective connectors on the interface board (see, e.g., FIG. 8B).

Improvements and modifications which become apparent to persons of ordinary skill in the art after reading this disclosure, the drawings and the appended claims are deemed within the spirit and scope of the present invention.

What is claimed is:

1. An X-ray imaging system comprising:

an X-ray image sensor;

a computing device; and an interface package including a first interface to the X-ray image sensor and a second interface to the computing device, wherein a sensor holder is integrated with the interface package to hold the X-ray image sensor when the sensor is not being used.

2. The X-ray imaging system of claim 1, wherein the sensor holder is integrated in one of the first interface or the second interface.

3. The X-ray imaging system of claim 1, wherein the interface package includes an electrical cable for coupling the first interface to the-X-ray image sensor.

4. The X-ray imaging system of claim 3, wherein the sensor holder is attached to the electrical cable.

5. The X-ray imaging system of claim 3, wherein
the first interface has a first connector and the electrical cable has a second connector,
the first interface and the electrical cable are detachably coupled through mating of the first connector and the second connector, and
the sensor holder is integrated with the second connector.

6. The X-ray imaging system of claim 1, wherein the interface package includes an electrical cable for coupling the second interface to the computing device.

7. The X-ray imaging system of claim 6, wherein the electrical cable is coupled to the computing device through a USB port of the computing device.

8. The X-ray imaging system of claim 6, wherein the sensor holder is attached to the electrical cable.

9. The X-ray imaging system of claim 6, wherein
the second interface has a first connector and the electrical cable has a second connector,
the second interface and the electrical cable are detachably coupled through mating of the first connector and the second connector, and
the sensor holder is integrated with the second connector.

10. The X-ray imaging system of claim 1, wherein the second interface includes a first wireless interface for communicating with a second wireless interface in the computing device.

11. The X-ray imaging system of claim 1, wherein the first interface includes a first wireless interface for communicating with a second wireless interface in the X-ray image sensor.

12. The X-ray imaging system of claim 1, wherein the X-ray image sensor is wireless and the interface package includes a charger for recharging the wireless X-ray image sensor.

13. The X-ray imaging system of claim 1, wherein the X-ray image sensor is wireless and the interface package includes a docking station for downloading data from the wireless X-ray image sensor.

14. The X-ray imaging system of claim 1, wherein the X-ray imaging system is a digital dental imaging system and the X-ray image sensor is an intraoral sensor.

15. An X-ray imaging sensor-interface package, comprising:
an X-ray image sensor;
an interface for connecting the X-ray image sensor to an X-ray imaging system; and
a sensor holder integrated with the interface to hold the X-ray image sensor when the sensor is not being used.

16. The X-ray imaging sensor-interface package of claim 15, wherein the sensor holder is shaped and sized to hold each of a plurality of different-sized sensors.

17. The X-ray imaging sensor-interface package of claim 15 further comprising an electrical cable coupled to the interface to connect the interface to the X-ray image sensor.

18. The X-ray imaging sensor-interface package of claim 17, wherein the sensor holder is attached to the electrical cable.

19. The X-ray imaging sensor-interface package of claim 17, wherein
the interface has a first connector and the electrical cable has a second connector,
the interface and the electrical cable are detachably coupled through mating of the first connector and the second connector, and
the sensor holder is integrated with the second connector.

20. The X-ray image sensor interface package of claim 15 further comprising an electrical cable for coupling the interface to the X-ray imaging system.

21. The X-ray imaging sensor-interface package of claim 20, wherein the sensor holder is attached to the electrical cable.

22. The X-ray imaging sensor-interface package of claim 20, wherein
the interface has a first connector and the electrical cable has a second connector,
the interface and the electrical cable are detachably coupled through mating of the first connector and the second connector, and
the sensor holder is integrated with the second connector.

23. The X-ray imaging sensor-interface package of claim 15, wherein the interface comprises a housing and a printed circuit board in an interior of the housing.

24. The X-ray imaging sensor-interface package of claim 23, wherein the printed circuit board has circuitry residing thereon for receiving electronic signals supplied by the X-ray image sensor and processing the received signals to communicate the processed signals to the X-ray imaging system.

25. The X-ray imaging sensor-interface package of claim 23, wherein the printed circuit board has circuitry residing thereon for receiving commands from the X-ray imaging system for controlling the X-ray image sensor.

26. The X-ray imaging sensor-interface package of claim 15, wherein the interface includes a first wireless interface for communicating with a second wireless interface in the X-ray imaging system.

27. The X-ray imaging sensor-interface package of claim 15, wherein the interface includes a first wireless interface for communicating with a second wireless interface in the X-ray image sensor.

28. The X-ray imaging sensor-interface package of claim 15, wherein the X-ray image sensor is wireless and the interface includes a charger for recharging the wireless X-ray image sensor.

29. The X-ray imaging sensor-interface package of claim 15, wherein the X-ray image sensor is wireless and the interface includes a docking station for downloading data from the wireless X-ray image sensor.

30. The X-ray imaging sensor-interface package of claim 15, wherein
the interface includes a first interface to the the X-ray image sensor and a second interface to the X-ray imaging system.

31. The X-ray imaging sensor-interface package of claim 30, wherein the sensor holder is integrated with the first interface.

32. The X-ray imaging sensor-interface package of claim 30, wherein the sensor holder is integrated with the second interface.

* * * * *